US006365567B1

(12) United States Patent
Nadakatti et al.

(10) Patent No.: US 6,365,567 B1
(45) Date of Patent: Apr. 2, 2002

(54) MELT CAST SOLID SHAPED DETERGENT BAR COMPOSITIONS WITH HIGH WATER CONTENT

(75) Inventors: Suresh Murigeppa Nadakatti; Vijay Mukund Naik; Shiju Thomas, all of Bangalore (IN)

(73) Assignee: Unilever Home & Personal Care USA, Greenwich, CT (US)

( * ) Notice: Subject to any disclaimer, the term of this patent is extended or adjusted under 35 U.S.C. 154(b) by 0 days.

(21) Appl. No.: 09/696,424

(22) Filed: Oct. 25, 2000

(30) Foreign Application Priority Data

Oct. 25, 1999 (IN) ........................................ 717/BOM/99

(51) Int. Cl.[7] ................................................ A61K 7/50

(52) U.S. Cl. ...................... 510/440; 510/446; 510/447; 510/481; 510/488

(58) Field of Search ................................ 510/447, 156, 510/481, 488, 440, 446

(56) References Cited

U.S. PATENT DOCUMENTS

| | | | | | |
|---|---|---|---|---|---|
| 4,165,293 | A | | 8/1979 | Gordon | |
| 4,201,743 | A | * | 5/1980 | Peria et al. | 264/148 |
| 5,340,492 | A | | 8/1994 | Kacher et al. | |
| 5,759,982 | A | * | 6/1998 | Wisev et al. | 510/352 |
| 5,916,856 | A | | 6/1999 | Massaro et al. | |
| 5,929,011 | A | | 7/1999 | Scepanski | |
| 5,968,892 | A | * | 10/1999 | Hutchins | 510/447 |

FOREIGN PATENT DOCUMENTS

| | | |
|---|---|---|
| EP | 0205999 | 12/1986 |
| EP | 0434460 | 6/1991 |
| WO | 96/04361 | 2/1996 |
| WO | 98/11864 | 3/1998 |

* cited by examiner

*Primary Examiner*—Necholus Ogden
(74) *Attorney, Agent, or Firm*—Ronald A. Koatz

(57) ABSTRACT

A melt cast solid shaped detergent bar composition comprising 2–60% of water insoluble structurant and 2–50 detergent active, characterized in that it comprises 0.5–30% of a salting in electrolyte and 30–80% water.

3 Claims, No Drawings

MELT CAST SOLID SHAPED DETERGENT BAR COMPOSITIONS WITH HIGH WATER CONTENT

The present invention relates to melt-cast solid shaped detergent compositions.

Detergent tablets are conventionally manufactured by one of the two methods: (i) shear working/homogenisation of the formulation followed by extrusion and stamping, or (ii) casting.

In the manufacture of detergent tablets by shear working and extrusion the amount of water that can be incorporated into the formulation is less than ~15%. These systems are multiphase composites which exhibit "bricks suspended in mortar" type of morphology. The bricks are solid particles, which in the case of toilet soaps are crystalline salts of long chain saturated fatty acids, inorganic fillers, etc. The mortar is a mixture of various lyotropic liquid crystalline or isotropic solution phases comprising water, liquid additives, and relatively water soluble soaps or surfactants. These compositions would typically comprise of 50–60% solids, 20–30% Lyotropic liquid crystalline phases and about 10% isotropic liquid.

In the manufacture of detergent compositions by casting the formulated system is taken to a fluid state by raising the temperature, filled into moulds, and cooled. This technology is commonly employed for manufacturing transparent personal wash tablets that contain among other ingredients (such as soap and synthetic surfactants) typically 15–50% of expensive components such as ethanol, polyhydric alcohols, sugars, etc at the time of casting. U.S. Pat. No. 4,165,293 (Amway, 1979); WO 96/04361 (P&G, 1996) discloses a solid transparent soap bar comprising soap, synthetic surfactants and a water soluble organic solvent such as e.g. propylene glycol. The level of water in these compositions is about 10–32%.

The problem in manufacturing non-transparent detergent tablets by casting is that the typical compositions do not form a pourable liquid at elevated temperatures. U.S. Pat. No. 5,340,492 (P&G, 1994) claims a castable composition having a three-dimensional skeleton structure comprising a relatively rigid, interlocking mesh of neutralised crystalline carboxylic acids (soap), synthetic surfactants and high levels of water and other liquids. However, the patent does not demonstrate the claims without employing about 15% propylene glycol in the composition.

The compositions claimed in U.S. Pat. No. 5,340,492 will be soft, exhibiting an yield stress of less than 75 kPa as measured using a cheese wire cutter apparatus, and hence can not be employed as firm tablets which are rigid enough to be conveniently held in hand for use. In order to increase the rigidity of the bar the examples in the patent employ ingredients such as polyols (e.g. propylene glycol) in the composition, under the guise of so called "bar appearance aids". The patent does not disclose any composition without the incorporation of "bar appearance aids" when synthetic surfactants are also present in the composition. These bar appearance aids are expensive and also reduce the amount and speed of lather.

The object of the present invention is to obtain solid shaped detergent compositions, with very high levels of water or liquid benefit agents, that are rigid and economical while maintaining good in-use properties.

It has now been found that the incorporation of low amounts of salting-in electrolytes in melt-cast detergent compositions comprising very high levels of water or liquid benefit agents result in rigid solid shaped articles exhibiting an yield stress greater than 75 kPa as measured using a cheese wire cutter apparatus. These compositions can be held in hand, are economical, high foaming and demonstrate good in-use properties.

Thus according to a first aspect of the invention, there is provided a melt-cast solid shaped detergent composition comprising:

a) 2–60% of a water insoluble structurant;

b) 2–50% of a detergent active species;

c) 0.5–30% of a salting-in electrolyte;

d) 30–80% water;

and optionally other liquid benefit agents.

According to a preferred aspect the invention relates to a melt-cast solid shaped detergent composition comprising:

a) 2–50% of a water insoluble structurant selected from saturated fatty acid soap comprising one or more of neutralised $C_6$–$C_{24}$ fatty acids, b) 2–40% of a detergent active species, c) 0.5–20% of a salting-in electrolyte, and d) 30–80% water and optionally other liquid benefit agents.

According to a more preferred aspect the invention relates to a melt-cast solid shaped detergent composition comprising:

a) 5–40% of a saturated fatty acid soap comprising one or more of $C_{12}$–$C_{24}$ fatty acids, b) 2–20% of a detergent active species, c) 0.5–15% of a salting-in electrolyte, and d) 35–70% water and optionally other liquid benefit agents.

It is preferred that the detergent active is predominantly non-soap.

According to another aspect of the invention there is provided a process for manufacturing the solid shaped detergent composition comprising the steps of:

a) making a melt of the above composition, b) pouring the said melt into a mould to obtain the desired shape, and c) cooling the mould under quiescent conditions to bring about solidification.

According to a preferred aspect of the invention there is provided a process for manufacturing cast-in-pack solid shaped detergent composition comprising the steps of:

a) making a melt of the above composition, b) pouring the said melt into a pre-formed polymeric mould to obtain the desired shape, c) sealing the mould, and d) cooling the mould under quiescent conditions to bring about solidification.

The present invention relates to melt-cast solid shaped detergent compositions that essentially comprise salting-in electrolytes, and a process for manufacturing the same.

The solid shaped articles of the composition according to the invention are rigid enough to be conveniently held in the hand, are economical, high foaming, and exhibit good in-use properties. The compositions exhibit yield stress values greater than 75 kPa as measured using the cheese wire cutter apparatus.

Salting-in electrolytes for use in the composition are selected from those listed in the 'Hofmeister' or 'Lyotropic' series. The salting-in electrolytes are generally those wherein the lyotropic number for the anion of the electrolyte is >10. Some examples of anions with lyotropic number >10 are $NO_2^-$, $ClO_3^-$, $Br^-$, $NO_3^-$, $ClO_4^-$, $I^-$, $CNS^-$, $C_6H_5SO_3^-$, $C_6H_4CH_3SO_3^-$ and $Cr_2O_7^{2-}$. The preferred examples of salting-in electrolytes for use in compositions according to the present invention are alkali metal salts of the above mentioned anions. The most preferred examples of the salting-in electrolytes for use in compositions according to the present invention are sodium toluene sulphonate, sodium cumene sulphonate and sodium xylene sulphonate. Further examples of salting-in electrolytes may be selected form those described in (i) Collins, K. D.; Washabaugh, M. W. Quart. Rev. Biophys., 1985, 18, 323; (ii) Schuster. P, Zundel. G and Sandorfy. C, 1976, 'The Hydrogen Bond', Recent developments in theory and experiments, Vol. III, North-Holland Publishing Co. Amsterdam, N.Y., Oxford.

Water insoluble structurants are preferably selected from saturated fatty acid soap comprising one or more of $C_6$–$C_{24}$ fatty acids. The term soap denotes salts of carboxylic fatty acids. The soap employed as water insoluble structurant may be a sodium, potassium, magnesium, aluminium, calcium or lithium salt of saturated fatty acids. It is especially preferred to have soap obtained as sodium or potassium salt of saturated fatty acid. The soap may be obtained from one or more of $C_{12}$–$C_{24}$ saturated fatty acids.

The water insoluble structurant in the composition is preferably 5–50% by weight and more preferably 5–40% by wt. of the composition.

The compositions according to the invention comprise detergent actives that may be soap or non-soap based. It is preferable to employ non-soap detergent actives that are selected from anionic, non-ionic, cationic, amphoteric or zwitterionic surfactants or their mixtures.

Suitable anionic detergent active compounds are water soluble salts of organic sulphuric reaction products having in the molecular structure an alkyl radical containing from 8 to 22 carbon atoms, and a radical chosen from sulphonic acid or sulphuric acid ester radicals and mixtures thereof. Some examples of synthetic anionic detergent active compounds are linear alkyl benzene sulphonate, sodium lauryl sulphate, sodium lauryl ether sulphate, alpha olefin sulphonate, alkyl ether sulphate, fatty methyl ester sulphonate, alkyl isothionate, etc. Other anionic surfactants are soaps, which may be selected from salts of unsaturated fatty acids such as oleic acid, ricinoleic acid, lauroleic acid, undecanoic acid, myristolic acid, palmitolic acid, erusic acid, linoleic acid, linolenic acid or a mixture thereof.

The cations most suitable in above detergent active species are sodium, potassium, ammonium, and various amines e.g. monoethanol amine, diethanolamine and triethanolamine.

Suitable nonionic detergent active compounds can be broadly described as compounds produced by the condensation of alkylene oxide groups, which are hydrophilic in nature, with an organic hydrophobic compound which may be aliphatic or alkyl aromatic in nature. The common nonionic surfactants are the condensation products of aliphatic alcohols having from 8 to 22 carbon atoms in either straight or branched chain configuration with ethylene oxide, such as a coconut oil ethylene oxide condensate having from 2 to 15 moles of ethylene oxide per mole of coconut alcohol. Some examples of non-ionic surfactants are alkyl phenol ethylene oxide (EO) condensate, tallow alcohol 10 EO condensate, alkyl de-methyl amine oxides, lauryl mono-ethanolamide, etc.

Some examples of amphoteric detergent active are coco amidopropyl betaine, cocobetaine, etc.

It is also possible optionally to include cationic or zwitterionic detergent actives in the compositions according to the invention.

Further examples of suitable detergent-active species are given in the following well-known textbooks: (i) "Surface Active Agents", Volume I by Schwartz and Perry, (ii) "Surface Active Agents and Detergents", Volume II by Schwartz, Perry and Berch, (iii) "Handbook of Surfactants", M. R. Porter, Chapman and Hall, New York, 1991.

The detergent active to be employed in the detergent composition of this invention is preferably anionic and will generally be up to 50% and more preferably from 2 to 30%.

According to a preferred aspect of the invention, liquid skin benefit materials such as moisturisers, emollients, sunscreens, anti ageing compounds are incorporated in the composition. Examples of suitable moisturisers and humectants include polyols, glycerol, cetyl alcohol, carbopol 934, ethoxylated castor oil, paraffin oils, lanolin and its derivatives. Silicone compounds such as silicone surfactants like DC3225C (Dow Corning) and/or silicone emollients, silicone oil (DC-200 Ex-Dow Corning) may also be included. Sun-screens such as 4-tertiary butyl-4'-methoxy dibenzoylmethane (available under the trade name PARSOL 1789 from Givaudan) and/or 2-ethyl hexyl methoxy cinnamate (available under the trade name PARSOL MCX from Givaudan) or other UV-A and UV-B sun-screens.

Other optional ingredients such as hair conditioning agents, fillers, colour, perfume, opacifier, preservatives, one or more water insoluble particulate materials such as talc, kaolin, polysaccharides and other conventional ingredients may be incorporated in the composition.

The process of manufacturing of the solid shaped detergent compositions according to the invention comprises following steps:

i. Mixing the components such as the water insoluble structurants, the detergent active, salting in electrolyte and water in a agitator/mixer at elevated temperatures of >50° C. to obtain a pourable melt.
ii. The melt is poured in to a rigid or flexible mould. It is preferred to use a near net shape flexible polymeric mould that is obtained in desired shape using e.g. thermoforming technology.
iii. The composition is allowed to cool in the mould to bring about solidification.
iv. The detergent article may be demoulded.

The mould may be suitably selected to produce near net shape tablet or to produce bars/blocks. The bars/blocks may be further shaped in to detergent article.

If the solid detergent article is produced using a near net shape thermoformed polymer, the mould is sealed to obtain a cast-in pack detergent composition. To obtain cast-in pack detergent composition the mould is preferably sealed immediately after filling the mould.

The invention will now be illustrated by way of example only with respect to the following non-limiting examples.

EXAMPLES

Preparation of the Composition:

A mixture containing fatty acids, non-soap detergent and salting-in electrolyte as given below was mixed in a two liter capacity round bottomed flask. The batch temperature was raised to 80° C. The aqueous solution of sodium hydroxide was added to the mixture to saponify the fatty acids. The batch temperature was maintained at 80° C. so that a clear solution was obtained. The melt of the soap at 80° C. was poured into a thermoformed polymeric mould and the inlet of the mould was sealed. The mould was allowed to cool to bring about solidification of soap and a cast-in-pack detergent composition was thus obtained. The above process of manufacture was used to prepare bars described in Tables 1 and 2. The rigidity of the bars processed was determined in terms of yield stress using the procedure described below.

The yield stress was measured using a 'cheese wire cutter' apparatus. The apparatus consists of a cheese wire attached to a counterbalanced arm that can pivot freely on a ball bearing. The billet of soap was positioned under the wire such that the wire was just in contact with the billet. A known weight was positioned directly above the cheese wire such that the wire sliced into the billet. The weight was removed after 1 minute and the length of the cut was measured using a vernier calliper. The yield stress (Y.S.) in Pascals (Pa) was calculated using the following formula:

$$Y.S. = \frac{3}{8}\frac{w \times 98.1}{l \times d}$$

where

1=length of cut, cm.

d=diameter of wire, cm w=weight over the cheese wire, g

TABLE 1

| | Component (% wt) | 1 | 2 | 3 | 4 | 5 | 6 |
|---|---|---|---|---|---|---|---|
| Structurant | Sodium Stearate | 12 | 12 | 12 | 20 | 20 | 20 |
| Detergent active | Sodium lauryl ether sulphate | 10 | 10 | 17 | 15 | 15 | 25 |
| Salting-in electrolyte | Sodium toulene sulphonate | 7 | 0 | 0 | — | — | — |
| | Potassium thiocyanate | — | — | — | 10 | 0 | 0 |
| Optional ingredient | Propylene Glycol | 0 | 0 | 0 | 10 | 10 | 10 |
| Water | Water | 71 | 78 | 71 | 45 | 55 | 45 |
| | Yield Stress (kPa) | 138 | 35 | 17 | 372 | 66 | 27 |

The data presented in Table 1 demonstrate that incorporation of salting in electrolytes with lyotropic number >10 in the detergent composition is essential to produce rigid tablets containing about 45–71% water exhibiting an yield stress >75 kPa, and thus can be conveniently held in hand for use. By contrast the compositions obtained without the salting in electrolytes are of pasty consistency and can not be held in hand as a rigid tablet for convenient use.

Table 2 shows several examples which demonstrate that incorporation of salting in electrolytes with lyotropic number >10 in the detergent composition is essential to produce rigid tablets exhibiting an yield stress >75 kPa. In the examples shown in Table 2 the compositions obtained without the salting in electrolytes (1*a*–12*a*) are of pasty consistency (yield stress <75 kPa) and can not be held in hand as a rigid tablet for convenient use. By contrast the compositions obtained using salting in electrolytes (1*b*–12*b*) are rigid exhibiting an yield stress of >75 kPa and thus can be conveniently held in hand for use.

TABLE 2(i)

| Component | 1a | 1b | 2a | 2b | 3a | 3b | 4a | 4b |
|---|---|---|---|---|---|---|---|---|
| Sodium stearate | 15 | 15 | 20 | 20 | — | — | 7.7 | 7.7 |
| Sodium palmitate | — | — | — | — | 15 | 15 | 9.4 | 9.4 |
| Sodium hydroxy stearate | — | — | — | — | — | — | — | — |
| Sodium myristate | — | — | — | — | — | — | — | — |

TABLE 2(i)-continued

| Component | 1a | 1b | 2a | 2b | 3a | 3b | 4a | 4b |
|---|---|---|---|---|---|---|---|---|
| Sodium laurate | — | — | — | — | — | — | — | — |
| Sodium behenoate | — | — | — | — | — | — | — | — |
| Sodium lauryl ether sulphate | 10 | 10 | 15 | 15 | 10 | 10 | 8.6 | 8.6 |
| Coco betaine | — | — | — | — | — | — | — | — |
| Coco amidopropyl betaine | — | — | — | — | — | — | — | — |
| Sodium oleate | — | — | — | — | — | — | — | — |
| Sodium ricinoleate | — | — | — | — | — | — | — | — |
| Sodium toulene sulphonate | — | 10 | — | — | — | 10 | — | 15 |
| Potassium iodide | — | — | — | — | — | — | — | — |
| Potassium thiocyanate | — | — | — | 10 | — | — | — | — |
| Sodium nitrate | — | — | — | — | — | — | — | — |
| Propylene Glycol | — | — | 10 | 10 | — | — | — | — |
| Water | 75 | 65 | 55 | 45 | 75 | 65 | 74.3 | 59.3 |
| Yield stress (kPa) | 48 | 154 | 66 | 372 | 75 | 103 | 25 | 230 |

TABLE 2(ii)

| Component | 5a | 5b | 6a | 6b | 7a | 7b | 8a | 8b |
|---|---|---|---|---|---|---|---|---|
| Sodium Stearate | 14 | 14 | 16 | 16 | 18.8 | 18.8 | 13 | 13 |
| Sodium Palmitate | — | — | — | — | — | — | — | — |
| Sodium hydroxy stearate | — | — | — | — | — | — | — | — |
| Sodium laurate | — | — | — | — | — | — | — | — |
| Sodium Behenoate | — | — | — | — | — | — | — | — |
| Sodium lauryl ether sulphate | 15 | 15 | 15 | 15 | 15.6 | 15.6 | — | — |
| Coco betaine | — | — | — | — | — | — | — | — |
| Coco amidopropyl betaine | — | — | — | — | — | — | 10 | |
| Sodium oleate | — | — | — | — | — | — | — | — |
| Sodium ricinoleate | — | — | — | — | — | — | — | — |
| Sodium toulene sulphonate | — | — | — | — | — | 10 | — | 7 |
| Potassium iodide | — | — | — | 15 | — | — | — | |
| Potassium thiocyanate | — | — | — | — | — | — | — | — |
| Sodium nitrate | — | 10 | — | — | — | — | — | — |
| Propylene Glycol | 2 | 2 | 4 | 4 | 8.3 | 8.3 | — | — |
| Water | 69 | 59 | 65 | 50 | 57.3 | 47.3 | 77 | 70 |
| Yield stress (kPa) | 27 | 141 | 22 | 274 | 25 | 230 | 18 | 96 |

TABLE 2(iii)

| Component | 9a | 9b | 10a | 10b | 11a | 11b | 12a | 12b |
|---|---|---|---|---|---|---|---|---|
| Sodium stearate | 6.8 | 6.8 | 14 | 14 | 10.8 | 10.8 | 16.2 | 16.2 |
| Sodium palmitate | 7.2 | 7.2 | — | — | — | — | — | — |
| Sodium hydroxy stearate | 2.2 | 2.2 | — | — | — | — | — | — |
| Sodium myristate | — | — | — | — | 2.2 | 2.2 | — | — |
| Sodium laurate | — | — | 4.4 | 4.4 | 2.2 | 2.2 | — | — |
| Sodium behenoate | — | — | — | — | 2.1 | 2.1 | — | — |
| Sodium lauryl ether sulphate | 30 | 30 | 30 | 30 | 30 | 30 | — | — |
| Coco betaine | — | — | — | — | — | — | 10 | 10 |
| Coco amidopropyl betaine | — | — | — | — | — | — | — | — |
| Sodium oleate | 4.3 | 4.3 | — | — | — | — | — | — |
| Sodium Ricinoleate | 2.2 | 2.2 | — | — | — | — | — | — |
| Sodium toulene sulphonate | — | — | — | 15 | — | 15 | — | 10 |
| Potassium iodide | — | — | — | — | — | — | — | — |
| Potassium thiocyanate | — | 15 | — | — | — | — | — | — |
| Sodium nitrate | — | — | — | — | — | — | — | — |
| Propylene Glycol | 15 | 15 | 15 | 15 | 15 | 15 | — | — |
| Water | 32.3 | 17.3 | 36.6 | 21.6 | 37.7 | 22.7 | 73.8 | 63.8 |
| Yield stress (kPa) | <15* | 204 | <15* | 279 | <15* | 100 | 32 | 200 |

*The product obtained is of pasty consistency and can not be held in hand as a rigid tablet for convenient use. The yield stress could not be determined since the Cheese wire cut through the sample of 4 cm thickness.

What is claimed is:

1. A melt cast solid shaped detergent bar composition comprising:

(a) 2% to 60% by wt. of water insoluble structurant;

(b) 2% to 50% by wt. non-soap detergent active;

(c) 0.5 to 30% by wt. of a salting-in electrolyte having a lyotropic number for an anion of the electrolyte which is greater than 10, wherein said anion of the electrolyte is selected from the group consisting of $NO_2^-$, $ClO_3^-$, $NO_3^-$, $ClO_4^-$, $I^-$, $CNS^-$, $C_6H_5SO_3^-$, $Cr_2O_7^{2-}$, toluene sulfonate, cumene sulfonate, xylene sulfonate and mixtures thereof;

(d) 30% to 80% by wt. water and wherein the composition exhibits yield stress values greater than 75 kPa as measured using the cheese wire cutter apparatus.

2. A composition according to claim 1, wherein the water insoluble structurant is a saturated fatty acid soap which comprises one or more neutralised $C_{12}$–$C_{24}$ fatty acids.

3. A composition according to claim 1, wherein said salting in electrolyte is selected from the group consisting of sodium toluene sulphonate, sodium cumene sulphonate, sodium xylene sulphonate and mixtures thereof.

* * * * *